United States Patent [19]

Tavlarides et al.

[11] Patent Number: 4,852,396

[45] Date of Patent: Aug. 1, 1989

[54] SELF-CALIBRATING ULTRASONIC MEASUREMENT OF DISPERSED PHASE VOLUMETRIC HOLDUP IN LIQUID/LIQUID DISPERSIONS

[75] Inventors: Lawrence L. Tavlarides, Fayetteville, N.Y.; Julio C. Bonnet, Los Chaguaramos, Venezuela

[73] Assignee: Syracuse University, Syracuse, N.Y.

[21] Appl. No.: 177,695

[22] Filed: Apr. 5, 1988

[51] Int. Cl.$^4$ ............................................. G01N 29/02
[52] U.S. Cl. .................................. 73/61.1 R; 73/597
[58] Field of Search ............................. 73/61.1 R, 597

[56] References Cited

U.S. PATENT DOCUMENTS

| | | | |
|---|---|---|---|
| 3,892,127 | 7/1975 | Cirulis et al. | 73/61.1 R |
| 4,080,837 | 3/1978 | Alexander et al. | 73/61.1 R |
| 4,236,406 | 12/1980 | Reed et al. | 73/61.1 R |
| 4,522,068 | 6/1985 | Smith | 73/597 X |
| 4,630,482 | 12/1986 | Traina | 73/597 |
| 4,656,869 | 4/1987 | Zacharias | 73/597 |
| 4,726,221 | 2/1988 | Tavlarides et al. | 73/61.1 R |

OTHER PUBLICATIONS

Bonnet et al., Determination of Disposed Phase Holdup in Agitated Extraction Units by Ultrasonic Technique 35th Canadian Chem. Eng. Conf., 58–62, Oct. 6, 1985.
Bonnet et al., Ultrasonic Technique for Dispersed--Phase Holdup Measurements, 26 ISEC Research 811, Apr. 1987.

Primary Examiner—Stewart J. Levy
Assistant Examiner—Joseph W. Roskos
Attorney, Agent, or Firm—Wall and Roehrig

[57] ABSTRACT

The fractional volumetric holdup $\phi$ of a dispersed phase in a two liquid dispersed phase system in a reactor is determined by measuring the travel time of ultrasonic pulses on a fixed path for the dispersed phase, and for the two liquids separately, and calcualted according to the relation $$\phi = \frac{C_2(C_1 - C^*)}{C^*(C_1 - C_2)}$$

where $C^*$, $C_1$, and $C_2$ are the sound velocities in the dispersed phase, the first liquid, and the second liquid. The pulses can be transmitted from a transmitter transducer straight through the contents of the reactor to a receive transducer, or can be reflected off a die or similar flat faced member back to the originating transducer. A sonic velocimeter is disposed along the reactor and draws out a quantity of the two-liquid system, and separates it into the first and second liquids. The sound velocity of each liquid is measured with ultrasonic transducers, and the dispersed phase holdup $\phi$ is calculated based on these measured velocities. This technique compensates for changes in the sound velocities which accompany ongoing physical and chemical changes in the respective phases.

5 Claims, 7 Drawing Sheets

SELF-CALIBRATING ULTRASONIC MEASUREMENT OF DISPERSED PHASE VOLUMETRIC HOLDUP IN LIQUID/LIQUID DISPERSIONS

BACKGROUND OF THE INVENTION

This invention relates generally to measuring methods and apparatus for measuring, and is more particularly directed to the measurement of the relative amounts of a first and second liquid, where one liquid is held up or suspended in a liquid/liquid dispersed phase system. The invention is also directed to a system in which the travel time of ultrasonic pulses through the liquid/liquid dispersion is employed to derive the fractional volumetric dispersed phase holdup of the two-liquid dispersed phase system.

The present invention is more closely related to self-calibrated continuous monitoring of the dispersed phase fractional volumetric holdup, and to the continuous monitoring of the separate liquid phases, which can, and are expected to, change chemically during the time that the liquids are being monitored.

The invention can be applied to liquid-liquid extractors of the types known as pulsed columns, vibrating plate columns, rotating disc contactors, multi-state stirred columns, Kunii columns, mixer-settlers, and a variety of other liquid-liquid extractors and processing vessels. The invention can be applied to tubular reactors with or without internal means to sustain primary dispersions through turbulent mixing.

Previously, the measurement of the dispersed phase fractional volumetric holdup in two-phase liquid systems has been attempted by such techniques as displacement, pressure differentials, direct sampling, light beam attenuation, and electroresistivity. While these approaches can be employed to derive a result, none of them permits estimation or monitoring of the dispersed phase fractional volumetric holdup under steady state process conditions or during transient conditions. Additionally, none of these techniques can be considered non-invasive or non-intrusive. Consequently, none has proved entirely effective for monitoring the dispersed phase fractional volumetric holdup for liquids within a reaction vessel.

The dispersed-phase fractional holdup is an important parameter in calculations of the efficacy of a chemical reaction or mass transfer in multi-phase liquids, as it corresponds to the relative mass transfer interfacial area in a two-phase liquid system. Real-time accurate knowledge of this quantity permits optimization of liquid flow rates to carry out the chemical reaction with minimal waste and consistent product.

Therefore, it would be desirable to achieve accurate, non-invasive, non-intrusive, on-line continuous measurement of this parameter, thereby permitting optimization of liquid flow rates to conduct the chemical reaction or mass transfer with minimal waste. Accurate knowledge of dispersed phase fractional holdup would also permit optimal direct computerized process control, to produce consistent quality product and maintain safety of operation.

One previous approach to ultrasonic measurement of this quantity employed a sound velocimeter that was immersed in the liquid/liquid dispersion. This technique had the drawback of interfering with the flow of liquids through the reactor vessel.

No previous technique provided for self-calibration by directly measuring the properties of the pure liquid phases during the ongoing process to establish optimal steady-state conditions.

OBJECTS AND SUMMARY OF THE INVENTION

Accordingly, it is an object of this invention to provide a method and apparatus for measuring the dispersed phase fractional volumetric holdup in an ongoing process involving a liquid/liquid dispersion, and which avoids the drawbacks of the prior art.

It is another object of this invention to provide a technique for measuring the dispersed phase fractional volumetric holdup in which the measurement is self-calibrating, non-invasive and non-intrusive.

It is still another object of this invention to provide such a technique in which the measurement devices are disposed externally of the process vessel, avoiding disturbance of flow patterns of the fluids within the process vessel and avoiding contact of the active surfaces of the measurement devices with possibly corrosive chemicals within the vessel.

The above objects are achieved by measuring the travel time of an ultrasonic pulse, over a fixed path, through the liquid/liquid dispersion, and comparing such travel time with the travel time of the ultrasonic pulse over the same path through each of the two liquids when in substantially pure form. The dispersed phase fractional volumetric holdup, expressed as the symbol $\phi$, is then calculated according to the relationship $$\phi = t^* - t_1/t_1 - t_2$$

where $t_1$ and $t_2$ are the travel times of the ultrasonic pulses through the pure form liquid phases, and $t^*$ is the travel time of the ultrasonic pulses through the dispersed phase system.

This measurement of $\phi$ is carried out with one or more ultrasonic transducers preferably disposed externally of the process vessel, but in acoustic communication with its contents. The ultrasonic pulses are produced in one of the transducers, and then either pass diametrically across the vessel to a pickup transducer or are reflected and return to the originating transducer. Thus, the transducer or transducers emit a train of ultrasonic pulses which traverse a predetermined path through the vessel contents. A circuit for electrically exciting the transducer or transducers and sensor circuitry for sensing the presence of the received pulses are connected to the transducers, and a device, e.g. an oscilloscope or a digital processor, is connected to the sensor circuitry to permit calculation of the pulse travel times $t^*$, $t_1$ and $t_2$, and then to carry out computation of the dispersed phase fractional holdup $\phi$ according to the above relation.

Thereafter the process is carried out using the two liquids with the one being dispersed as very small droplets in the other. The travel time $t^*$ of the ultrasonic pulses through the dispersion is monitored continuously or on a periodic basis through the process, and the dispersed phase holdup $\phi$ is continuously computed. Process feed rates or other suitable parameters can be controlled to keep the fractional holdup value $\phi$ optimal. If the process temperature is expected to fluctuate, various values of $t_1$ and $t_2$ can be stored, for several respective temperatures, to account for temperature variations in the speed of acoustic waves through the liquids.

In a favorable embodiment the process reactor vessel is a column having baffles spaced along its axis to divide the column into compartments, and a mixing arrangement for dispersing the fluids includes a rotating shaft with at least one turbine impeller disposed within each such compartment. In one version, the shaft diameter is smaller than the diameter of the radiating element of the emitting transducer, so that the presence of the shaft does not obstruct the path of the ultrasonic pulses. In another version where the impeller shaft is of large diameter, flat-faced members, e.g. cubes or dice, are incorporated into the shaft to reflect the pulses back to the transducer. In this version, a synchronizer matches the timing of the ultrasonic pulses with the shaft rotations, so that the dice will be properly positioned to reflect the ultrasonic pulses back to the transducer.

For optimal results, it should be observed that the velocity of ultrasound pulses in liquid dispersions is linearly related to the dispersed phase fractional volumetric holdup $\phi$ where the dispersed liquid droplets are of a dimension as large as or larger than the ultrasound wavelength. That is, the ultrasound frequency is selected so that the wavelength is somewhat less than the expected dispersed phase droplet size.

It should be seen that the dispersed phase volumetric holdup $\phi$ can be continuously monitored, and that the monitoring does not interfere with the process operation. The liquids do not contaminate or corrode the ultrasonic transducers, as the transducers are disposed outside the vessel. It is unnecessary to measure or know the path length per se, for the ultrasonic pulses, as the value of the fractional holdup $\phi$ depends only on the differences in the overall travel time of the ultrasound pulses.

A preferred embodiment of this invention incorporates a method and apparatus for determining ongoing real-time data relative to dispersed-phase holdup on a reacting multi-phase fluid system. In such a system aqueous and organic phases of the two-phase system are separately tested, using sonic velocimeters, to derive more accurate measurements of the aqueous and organic sound velocities for use in the ultimate calculation of dispersed-phase fractional holdup.

According to this invention, the two-phase dispersion that is flowing in the reactor vessel is sampled on a continuous or periodic basis, and the phases are separated or allowed to separate. The speed of sound is measured in both the separated uncontaminated organic and aqueous phases. The measurements are carried out in dual differential sonic velocimeters, independently but substantially simultaneously, while the speed of sound of the dispersion is measured in the vessel. The separate speed of sound measurements are applied to electronic data processing circuitry, with appropriate programming, in which the dispersed phase fractional volumetric holdup is calculated, e.g., according to a relationship $$\phi = \frac{C_2 (C_1 - C^*)}{C^* (C_1 - C_2)}$$

where $C_1$ and $C_2$ are the speed of sound of ultrasonic pulses through the first and second (pure) liquid phases and $C^*$ is the speed of sound of the ultrasound pulses through the dispersed phase system.

The detected values of the holdup fraction $\phi$ at different locations in the reactor vessel may be displayed continuously on a monitor and the data can be fed to a recorder, and used in a computer to execute on-line direct digital control, for example, of the feed rates of the two phases into the vessel.

The above and many other objects, features, and advantages of this invention will be more fully understood from the ensuing detailed description of certain preferred embodiments, which is to be read in conjunction with the accompanying Drawing.

DETAILED DESCRIPTION OF THE PREFERRED EMBODIMENT

Figure 1:
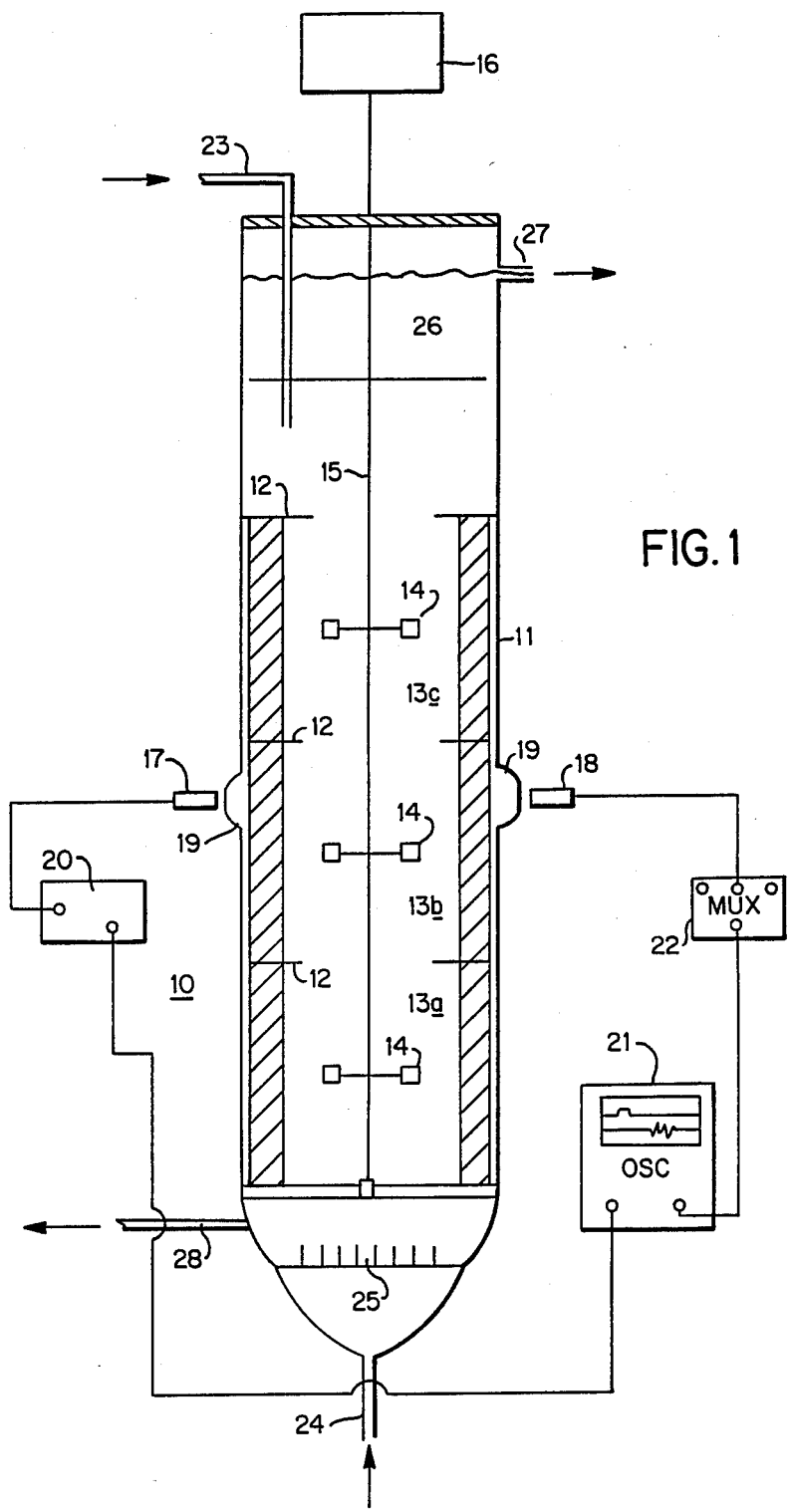
FIG. 1 is a schematic view of an extraction column arranged according to a first embodiment of this invention.

With reference to the drawing, and initially to FIG. 1 thereof, a continuous extraction reactor 10 is formed of a glass pipe column or vessel 11 ten cm in diameter and fifty cm high with baffles 12 along its axis dividing the vessel interior into fully baffled, agitated compartments 13a, 13b, 13c. Mixing of two liquid phases in counterflow within the column 11 is carried out mechanically by means of three turbine impellers 14, here of 33 mm diameter, mounted on a 9.5 mm shaft 15 at the axis of the vessel 11. The shaft 15 is rotationally driven by a 1/16 horsepower electric motor 16. The turbine impellers 14 are positioned centrally at each compartment 13a, 13b, 13c.

Two piezoelectric ultrasonic transducers 17 and 18 are located outside the vessel, each having an operative face against a respective flared flat ground-glass window 19. The windows 19 are situated diametrically opposite one another so that the transducers 17 and 18 face one another on a horizontal plane. The ultrasonic transducers 17 and 18 are in acoustic communication, through these windows 19, with the contents of the vessel 11. The transducers 17,18 have their natural frequency in the range of 0.5 MHz to 1.0 MHz and the diameter of the operative or radiating face of the transducers is about 1.2 to 2.5 cm.

A pulse generator 20 is connected to the transducer 17, which serves as the transmitting element, and is also connected to one channel of a four-channel oscilloscope 21. The other transducer 18, which serves as the receive element, is connected through a multiplexer 22 to another channel of the oscilloscope 21. While not shown here specifically, there can be pairs of transducers 17,18 and windows 19 at each of the compartments 13a, 13b, 13c, and the multiplexer 22 lets the oscilloscope 21 display the traces of the receive transducers 18 at each level, so the fractional holdup $\phi$ can be monitored at different column heights.

An aqueous feed 23 and an organic feed 24, supplied from respective peristaltic pumps, introduce the first and second liquids into the column 11 above the compartment 13c and below the compartment 13a, respectively. A relatively light organic dispersed phase enters the column 11 through a multi-hole glass distributor plate 25 located just below the bottom agitated compartment 13a. The coalesced organic dispersed phase collects at a top portion 26 of the column 11, and is removed via an overflow outlet 27. The processed aqueous continuous phase flows out by gravity through an outlet 28 at the bottom of the column.

Once the two liquid phases are dispersed by motion of the impellers 14, the pulse generator 20 is turned on and this feeds a train of rectangular pulses of adjustable width and frequency to the transducer 17. The latter in turn emits a train of ultrasonic pulses. These ultrasonic pulses travel through the dispersion and are received at the receive transducer 18, where they are converted into electrical output signals. The transducer output signals are then amplified and displayed on the oscilloscope 21. The pulse generator 20 also sends the pulse train to the oscilloscope to trigger the oscilloscope horizontal sweep. Thus, both the signal applied to the transmitter transducer 17 and the signal produced at the receiver transducer 18 are displayed simultaneously on the oscilloscope screen. The calibrated delay sweep of the oscilloscope is used to measure the travel time t* of the pulse-through ultrasonic pulses.

To calibrate for the travel times $t_1$ and $t_2$, the column is filled first only with the aqueous phase and then only with the organic phase, and the same procedure is used to read the respective travel times $t_1$ and $t_2$ on the oscilloscope 21. Once these values are established, they can be used for the continuous calculation of the fractional holdup value $\phi$, using the relationship mentioned above.

Figure 2:
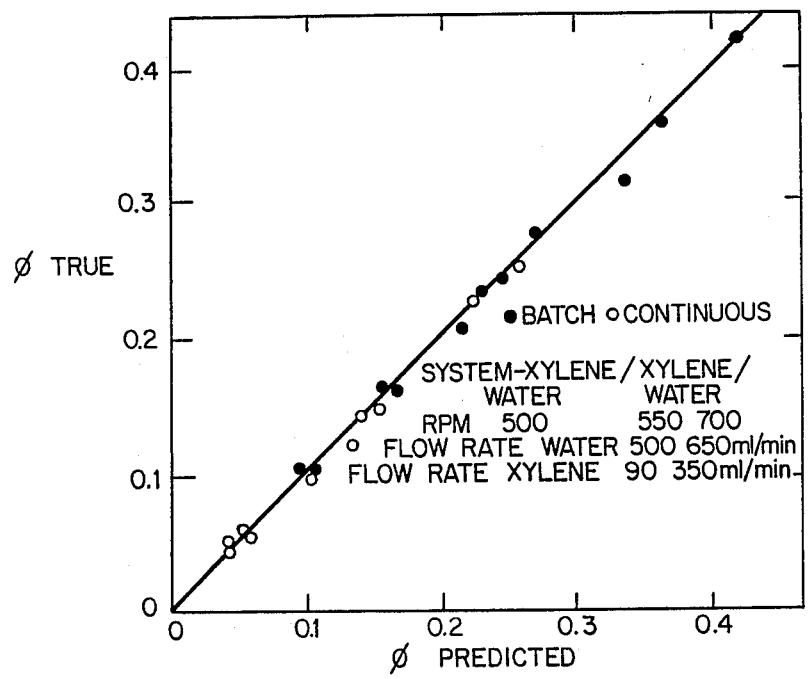
FIG. 2 is a chart showing experimental versus predicted results in the extraction column of FIG. 1 and in a batch reactor (not shown).

The results of fractional holdup measurement using this technique match very closely the results obtained using the more traditional "displacement" technique. The latter involves simultaneously closing off all feeds 23,24 and outlets 27,28 to and from the extraction column, and then measuring the volume of the coalesced dispersed phase collected in one of the column ends. The results of this comparison are shown with the open circles in FIG. 2. The results of this technique in a batch process vessel were also compared with results of batch process agitation in a glass beaker of 10 cm diameter, 10 cm height, with a centrally located agitator shaft and a turbine impeller, and with four metal baffles of 1 cm width disposed at 90 degree intervals. The results of this comparison are also shown in FIG. 2 with the black circles.

The presence of a solute or solutes in either phase may affect the velocity of sound in the dispersion. However, this technique is still quite valid if calibration curves for both single liquid phases are obtained, to permit compensation of the values of $t_1$, $t_2$ and t* for concentration effect. Similarly, if the process is non-isothermal, temperature compensation for sound velocity is required. This can be done by measuring and storing values of $t_1$ and $t_2$ over several temperatures of interest.

The positioning of the shaft 15 at the axis of the column 11, i.e., directly in the middle of the acoustic path, does not interfere with the preparation of the ultrasound pulses, and thus does not affect the measurement of the travel time t*. This lack of interference comes about at least in part because the diameter of the radiating face of the transducer 17 is larger than the diameter of the shaft 15. If the diameters were of comparable size, or the shaft diameter greater than the face diameter, then an alternative approach should be taken, such as the following.

Figure 3:
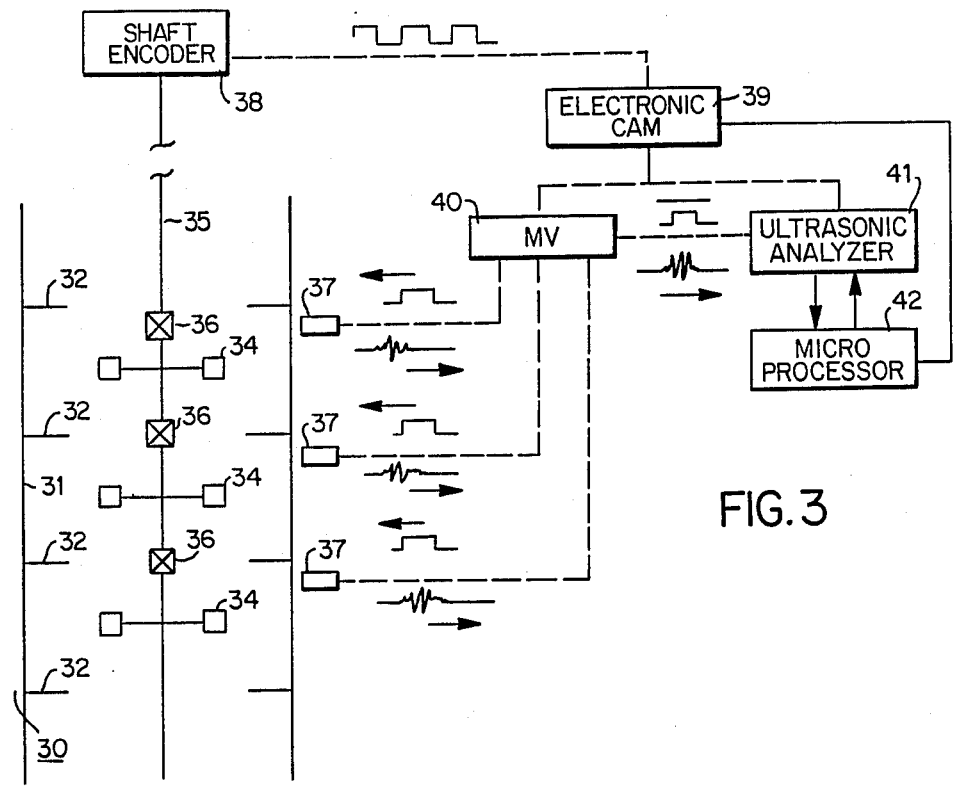
FIG. 3 is a schematic view of a reactor incorporating a second embodiment of this invention.

FIG. 3 illustrates a process reactor 30 according to a second embodiment of this invention which similarly to the first embodiment, has a glass reactor column or vessel 31 with baffles 32 that divide the interior of the column into a number of compartments 33, and with turbine impellers 34 mounted on a rotating shaft 35 disposed on the central axis of the column 31. In this embodiment, the diameter of the shaft 35 is larger than in the previous embodiment, and it significantly interferes with the ultrasonic wave front and renders the system acoustically opaque to straight-through sound transmission. In order to avoid that problem, a pulse echo technique is employed. This technique applies generally the same principles as the pulse through transmission technique, but the ultrasound pulses emitted by the transducer are totally reflected by a substantially flat surface on the shaft itself and the echoes are received either by the same transducer or by a receiver transducer disposed at or in the vicinity of the location of the transmitter transducer.

To effect this, cubes or dice 36 are mounted to rotate with the shaft 35. These dice 36 are made of a material of acoustic impedance Z much greater than the acoustic resistance $Z_1$ of the fluid contents of the column 31, that is $Z_2 >> Z_1$, or more specifically $Z_2/Z_1 \geq 30$.

Dual element transducers 37 are disposed outside column 31 at the levels of each of the dice 36 and facing towards the shaft 35.

To ensure that the transducers 37 are energized at the times that the dice 36 are oriented facing them, an incremental shaft encoder 38 is mounted on the shaft 35 and supplies shaft synchronization pulses to an electronic cam 39. The latter provides a channel select signal and pulse trigger signals to a multiplexer 41 which sends actuating pulses to each of the transducers 37. This system ensures synchronization of the ultrasound pulses with the shaft position, such that the arriving wavefront of the ultrasound pulses strikes the cubes or dice 36 when the flat face thereof is normal to the acoustic path, and the pulses are reflected back with a maximum energy to the receive elements of the transducers 37.

An ultrasonic analyzer 41 is connected to the multiplexer 40 and to the electronic cam 39 to sense the returned echo pulses, and a microprocessor control 42 is connected to the analyzer 41 and to the cam 39 to control the measurement process automatically, and also to automatically measure the ultrasound pulse travel time t* and compute the dispersed phase fractional volumetric holdup $\phi$. The electronic cam 39 is a solid state digital electronic circuit that converts the angular position of the shaft (as based on pulses from the shaft encoder 38) into a series of channel select and channel fire signals.

The operation of the reactor 30 of FIG. 3 is similar to that of FIG. 1. The transmitter/receiver ultrasonic transducer 37 emits an electronic pulse upon stimulation by a voltage pulse signal from the multiplexer 40 and ultrasonic analyzer 41. The pulse travels through the dispersion in the vessel 31 until it is reflected at the liquid-dice interface. Then, the reflected pulse travels back through the dispersion and is converted to an electrical signal by the transducer 37. This signal is channeled through the multiplexer 40 to the ultrasonic analyzer where it is amplified. The time difference between the transmitted and detected pulses is calculated in the microprocessor 42, the time difference, i.e. $t^*$, being the travel time of the pulse along the round-trip path in the dispersion.

This value of travel time $t^*$ is simply fit into the above equation, together with values of travel time $t_1$ and $t_2$, similarly measured for pulses through the pure liquids, and the dispersed phase fractional volumetric holdup $\phi$ is computed.

The description that follows relates to measurement apparatus and method for self-calibrating the system, and accommodating changes in composition and temperature of the liquid phases in the dispersion. The technique substantially avoids interference or obstruction of flow patterns of the fluids within the process vessels.

It should be explained at this point that although the path length for measurement of the times $t_1$, $t_2$, and $t^*$ is fixed, the actual composition and physical properties of the individual liquid phases will change as a result of the reaction or mass transfer operation. The velocity of sound $C^*$ of the dispersion will vary with the composition of the individual liquid phases, and the temperature of those phases during the process. The system is further complicated by the fact that the species concentration in each liquid phase will vary and the temperature profiles will develop during contacting of the two phases in the extractor column, due both to physical mass transfer and to chemical reactions associated with mass transfer.

This complication is resolved by providing, along the column, means for measuring the sound velocities of the aqueous phase and of the organic phase that are actually flowing in the dispersion. Then these two velocities are operated on to compute the actual fractional volumetric holdup $\phi$ from the velocity of sound $C^*$ in the aqueous-organic suspension. With this feature, the system becomes self-calibrating.

Figure 4:
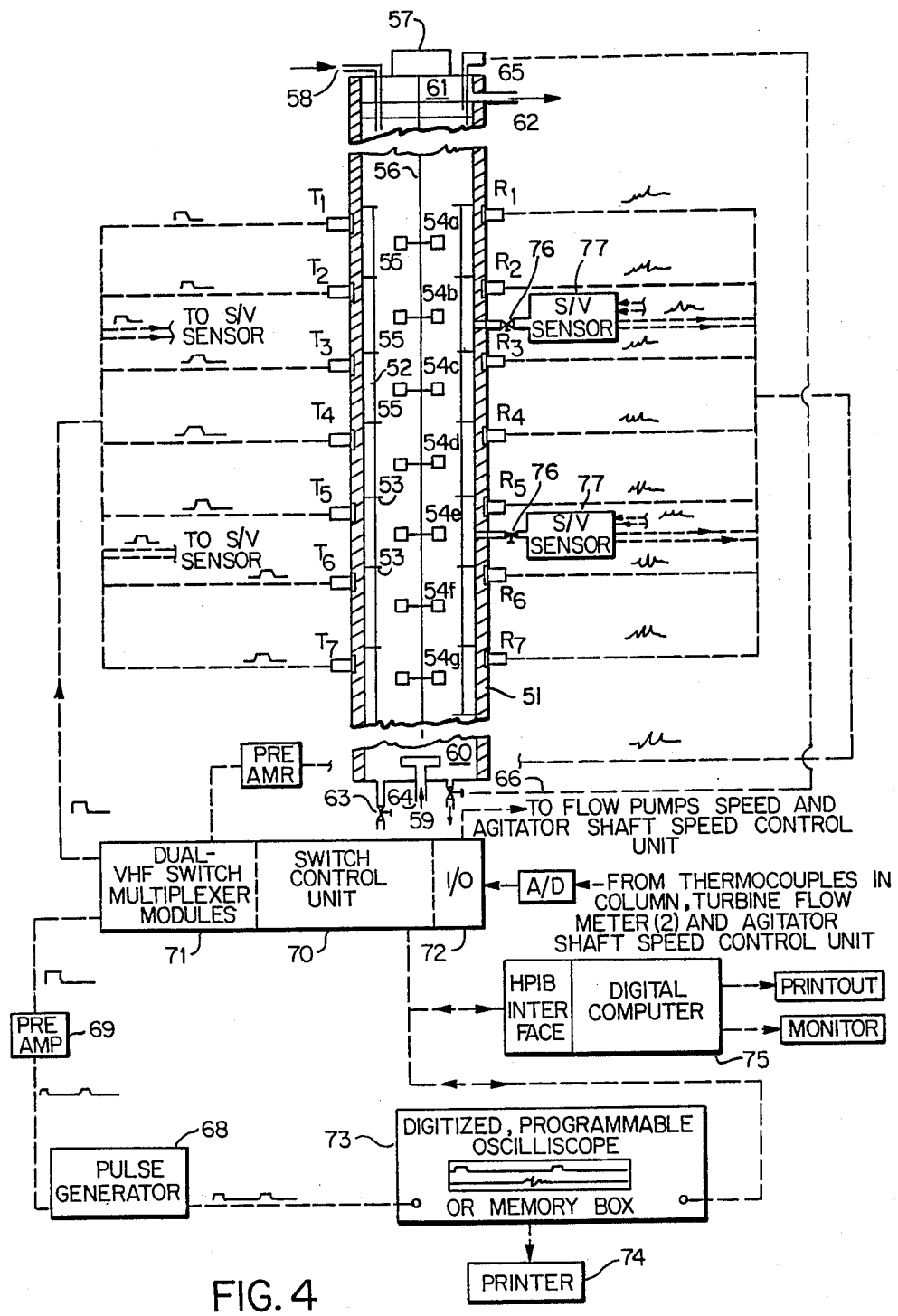
FIG. 4 is a schematic view of an extraction column arranged according to a third embodiment of this invention.

FIG. 4 illustrates a continuous liquid-liquid extraction apparatus 50 formed of a glass pipe or column 51, 12.5 cm in diameter and 110.0 cm high with stainless steel baffles 52 along its axis. Horizontal stainless steel baffles 53 divide the column interior into fully baffled agitated compartments 54a, 54b, 54c, 54d, 54e, 54f and 54g, each 12.5 cm high. Formation of the dispersion of the two immiscible liquid phases in counterflow within the column 51 is accomplished mechanically by means of seven turbine impellers 55, here each of 6.8 cm diameter, mounted on a 0.95 cm diameter shaft 56 located at the center of the column 51 and rotationally driven by a DC half-horsepower electric motor 57.

An aqueous feed 58 and an organic feed 59, supplied from respective peristaltic pumps, introduce the first and second liquids into the column 51 at the top and at the bottom of the column, respectively. A relatively light organic dispersed phase enters the column 51 through a multi-nozzle, polyfluorinated hydrocarbon and stainless steel distributor plate 60 disposed at the bottom of the column 51. The processed and coalesced organic dispersed phase collects at a disengagement section, or top portion 61 of the column 51 and is removed via an overflow outlet 62. The processed aqueous continuous phase flows out by gravity through outlets 63 and 64 at the bottom of the column.

The liquid-liquid interface in the disengagement section 61 is sensitive to changes in the operating conditions and physical properties. A specially designed liquid interface control system 65 maintains a constant interface level by sensing the electrical conductivity of the aqueous phase and controlling a portion of the aqueous stream discharge rate with the solenoid valve 66.

Seven pairs of piezoelectric ultrasonic transducers $T_1$, $R_1$; $T_2$, $R_2$; $T_3$, $R_3$; $T_4$, $R_4$; $T_5$, $R_5$; $T_6$, $R_6$ and $T_7$, $R_7$ are disposed on the outside surface of vessel 51, each transducer having its operative face against a respective flat, smooth polished window 67. The transducer windows 67 in each pair are situated diametrically opposite one another so that the transducers in each pair face one another on a horizontal plane. The ultrasonic transducers of each pair are in acoustic communication through the windows 67 with the two-phase dispersions in the column 11. The seven pairs of transducers have their central frequency in the range of 0.2 MHz to 5.0 MHz and the diameter of the radiating transducer face is in a range of about 1.0 to 12.5 cm. The transducers identified with the letter T are the transmit transducers responsible for sending the ultrasonic pulses and the transducers with the letter R are the receive transducers which translate the ultrasound pulses into voltage pulses.

The transmitting and receiver transducers pairs are electrically coupled to a data acquisition system consisting of a pulse generator 68, a wideband preamplifier 69, a fully programmable switch/control unit 70 with four dual four-channel VHF switch modules 71 and a sixteen-channel digital input/output module 72, a 200-megasample per second memory box or digitizing programmable oscilloscope 73, a printer 74 and a digital computer 75 with its associated peripherals.

Figure 5:
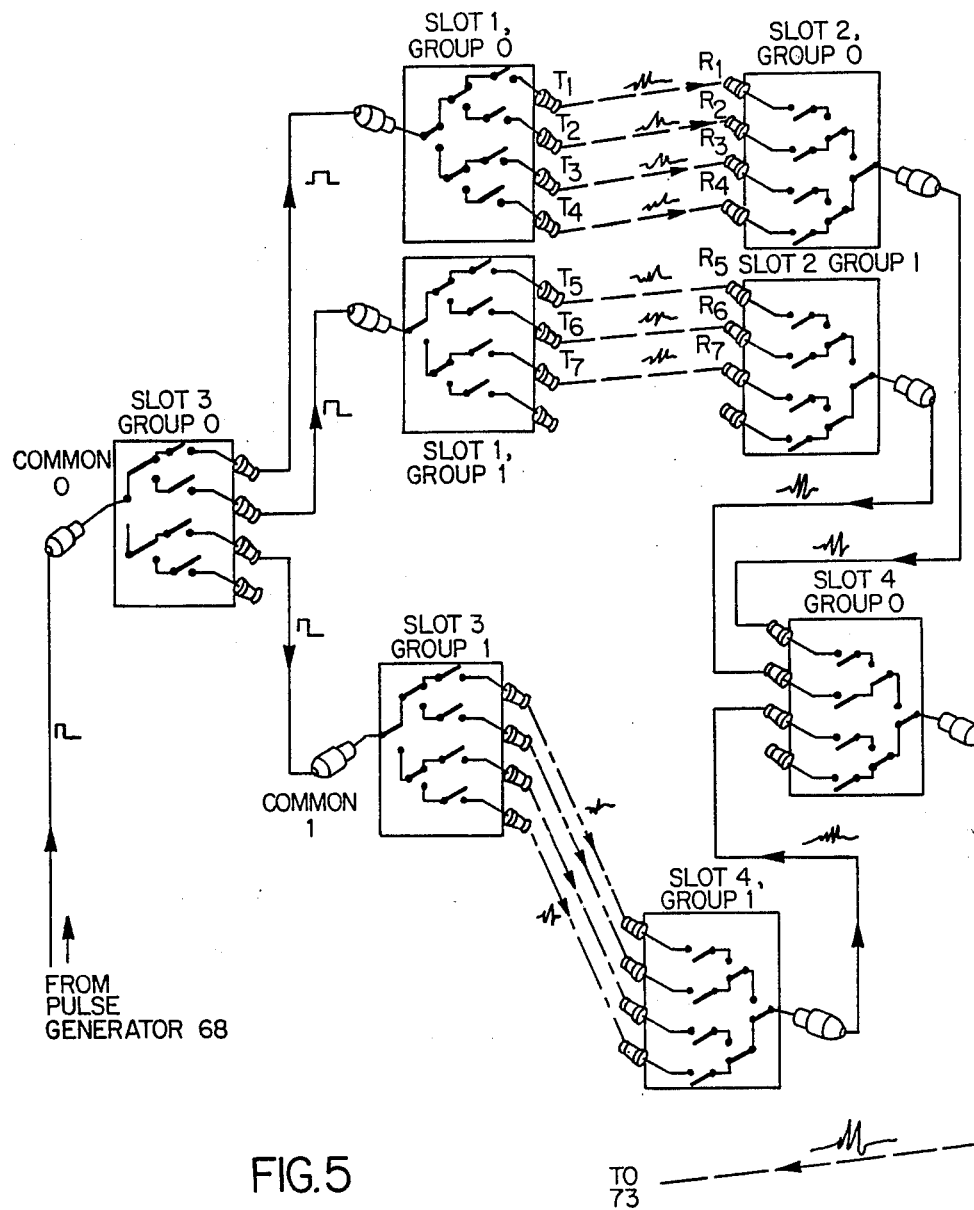
FIG. 5 is a schematic view of a VHF switching arrangement employed in this embodiment.

FIG. 5 shows the topology of the four VHF switch modules or cards 71 which connect the seven transducer pairs $T_1-T_7$, $R_1-R_7$ in the column and the four transducer pairs in the sonic velocimeters to be described later with the pulse generator 68 and the oscilloscope (or memory box) 73. Each of the four cards in the switch control unit, identified as Slot 1, Slot 2, Slot 3 and Slot 4, consists of a pair of independent 4-to-1 multiplexers identified as Group 0 and Group 1. Each Group in a card has four channels and it may be used as 1-of-4 inputs to one output or one input to 1-of-4 outputs with the connections being made through ten BNC coaxial connectors. Each channel can be accessed individually or in a predetermined scanning procedure by appropriate software in the computer 75. Channel addresses can be three digit number, e.g., channel 201 can mean slot 2, group 0 and channel 1. To interrogate a transducer pair like $T_2$-$R_2$ the sequence is, close channel 300, close channel 101, close channel 201, close channel 400. In this manner an electrical pulse from the pulse generator 68, after being amplified in preamplifier 69, is applied to the transmitter transducer $T_2$ which emits an ultrasonic pulse that travels through the column 51 and the liquid dispersions to be picked up by the receiver transducer $R_2$ and translated into an electrical pulse, this pulse is displayed and stored in the oscilloscope memory ready to be transferred to the computer for signal analysis and recognition. At the same time, the pulse generator 68 sends an identical voltage pulse to one of the oscilloscope channels to trigger the oscilloscope horizontal sweep. Various ways of measuring the overall transmission time of the ultrasound pulses are possible according to the analysis of the output electrical signal, which uniquely defines the pulse overall time of flight.

The overall pulse transmission time is the sum of the time interval the ultrasonic pulse spent crossing the dispersion plus the overall time delay which is the time interval consumed in passing through the electronics, acoustic windows and shaft delay, if a shaft is located in the acoustic path. To determine exactly the velocity of sound $C^*$ in the dispersion, it is necessary to determine the exact length of the sonic path through the liquid and the exact value for the overall time delay. These two parameters are prior determined by calibration of each transducer pair in the column using pure (degassed and distilled) water at different temperatures with reference to published sound velocity -temperature tables. The values of the above two parameters for each transducer pair in the column are included in the software program in the computer 75 to calculate the value of the speed of sound $C^*$ in the liquid dispersion.

(1) In order to calculate the fractional volumetric holdup $\phi$ of the dispersion using the relationship $$\phi = \frac{C_2(C_1 - C^*)}{C^*(C_1 - C_2)} \quad (1)$$

and employing a self-calibrating apparatus and technique, it is necessary to have the values of $C_1$ and $C_2$ in each liquid phase along the column. This should be done without having to measuring the species concentration profiles and temperature profile, and without numerous and impractical sound velocity—species concentration—temperature correlation curves. To achieve this highly desirable self-calibrating feature, two-phase dispersion samples are removed from the column 51 via a manually or electrically controlled valve 76 as shown in FIG. 4. The samples are permitted to separate in the sonic velocimeters 77 where the velocities of sound $C_1$ and $C_2$ in the individual organic and aqueous phases are measured.

Figure 6:
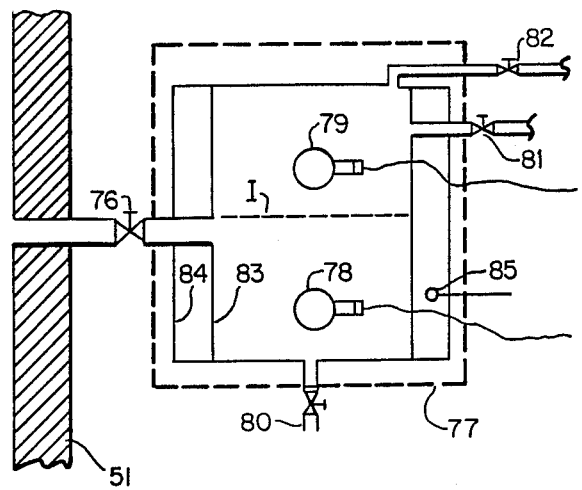
FIGS. 6 and 7 are a side elevation and a top plan view, respectively, of a sonic velocimeter as employed with this embodiment.
Figure 7:
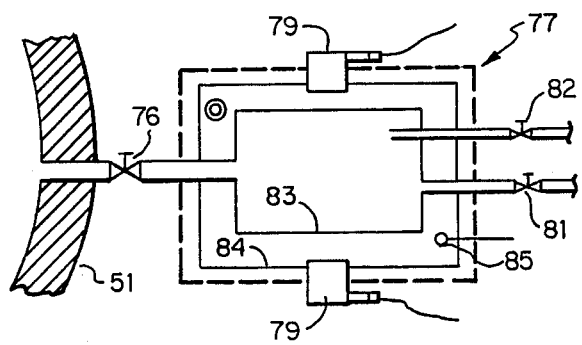

FIG. 6 is a schematic elevation of the thermally insulated differential dual sonic velocimeter 77 connected to the column 51 as shown in FIG. 4. FIG. 7 is a plan view of the same velocimeter showing the details of the internal construction of the instrument. The velocimeter 77 is a modified version of a differential sonic velocimeter developed earlier by the inventors and described at the 35th Canadian Chemical Engineering Conference, Oct. 6-9, 1985, Calgary, Alberta, Canada. A two-phase sample drawn from the column 51 through valve 76 goes into an internal receptacle 83 which is located inside a main receptacle 84 in such a position that its major surface areas lay parallel to the face of the two transducer pairs 78 and 79, as shown in FIG. 7. The space between receptacles 83 and 84 is kept filled with pure distilled and degassed water. By appropriate operation of valves 76, 80, 81 and 82 the organic and aqueous phases can be separated with an interface or boundary surface situated at a level between the transducer pairs 78 and 79. This defines an organic-filled upper chamber and an aqueous-filled lower chamber. The velocity of sound in the organic and aqueous phases is measured with an ultrasound propagation technique extensively detailed in the Proceedings of the 35th Canadian Chemical Engineering Conference. The difference in travel time of the sound pulse when the rectangular receptacle 83 is filled with degassed and distilled water and with the liquid phases sample is used in the following equation $$\Delta t = \frac{L_2}{C_{water}} - \frac{L_2}{C_{sample}} \quad (2)$$

to calculate the sound velocity in the organic and aqueous samples, $C_{sample}$ (i.e., $C_1$ and $C_2$). The travel times of sound pulses, when receptacle 83 is filled with water at different temperatures, are determined prior to the installation of the differential velocimeter 77 and those values along with the value of $L_2$, the length of the acoustic path inside receptacle 83, are included as data stored in the computer 75 which processes the information regarding pulses travel times. The differential dual velocimeter is thermally insulated with a temperature sensor 85 situated in the water-filled space between the main and inner receptacles 83, 84 and electrically connected to the I/O module 72 of the switch control unit 70. Exit port through-valves 80, 81, and 82 discharge the separated liquid samples into a common storage vessel (not shown), or recycle the same into the system. The values of the sound velocity $C_1$ in the organic phase and sound velocity $C_2$ in the aqueous phase are used in conjunction with sound velocity in the dispersion $C^*$ in equation (1) to calculate the fractional volumetric holdup $\phi$.

Figure 8:
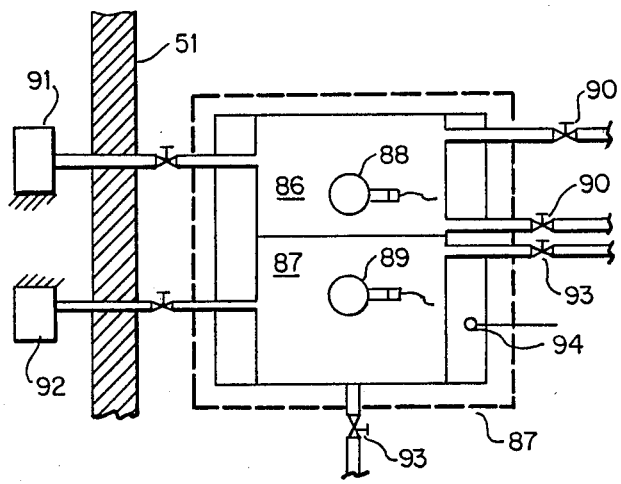
FIG. 8 is a side elevation of an alternative sonic velocimeter.

For those chemical systems and operating conditions which result in high mass transfer and kinetic rates, the time for separation of the phases in the velocimeters 77 could be excessively long. In such case, the concentration in the velocimeter 77 of the species in each phase could be drastically different from the corresponding concentration inside the column agitated compartment 55 from which the samples were withdrawn. Under this condition the use of equation 1 with the sound velocity of each of the pure phases can lead to erroneous values of $\phi$. In these cases a differential dual sonic velocimeter of the type presented in FIG. 8 is used. This velocimeter of two separate internal receptacles 86 and 87 to hold the uncontaminated samples of the individual organic and aqueous phases withdrawn from the column 51 by a coalescing head probe 91 for withdrawing the dispersed phase and a filter-type head probe 92 for withdrawing the continuous aqueous phase. These probes 91 and 92 can be constructed as proposed in J. C. Bonnet and G. V. Jeffreys, J., 33 Chem. Tec. and Biotech. 176, 1983, and P. M. Bapat and L. L. Tavlarides, 23 Ind. Eng. Chem. Fundl. 120, 1984. The probes 91, 92 are positioned inside the column 51. The rest of the differential velocimeter of FIG. 8 is the same the two phase sample differential velocimeter of FIG. 6, as is the procedure to obtain the sample using valves 90 and 93, and the procedure to find the sound velocity data of the individual phases.

The probes 91, 92 can have a filter formed of a hydrophobic or hydrophilic material so as to collect and pass the dispersed phase and reject the aqueous phase, or to collect and pass the aqueous phase and reject the dispersed organic phase. These filters can take the form of pile or brush members formed of a material which readily wets with one of the organic and aqueous phase, but not the other. The probes also have openings oriented downwards to catch the rising organic phase or upwards to catch the falling aqueous phase. Alternatively, a centrifuge device (not shown) can be used to separate the phases.

The above described ultrasonic technique is applicable in those apparatuses in which the ratio of the diameter of the transducer radiating element to the diameter of the rotating shaft is sufficiently large as to produce a sharp signal in the receiver transducer or in those apparatuses, such as pulse columns and spray columns, where no shaft is in the acoustic path. When the ratio of the transducer element diameter to shaft diameter tends towards unity, the system may become acoustically opaque to straight-through sound transmission or th shape of the received signal may become so aberrated that signal-recognition capability is impossible or impracticable. In these cases the alternate technique shown in FIG. 9 should be used.

Figure 9:
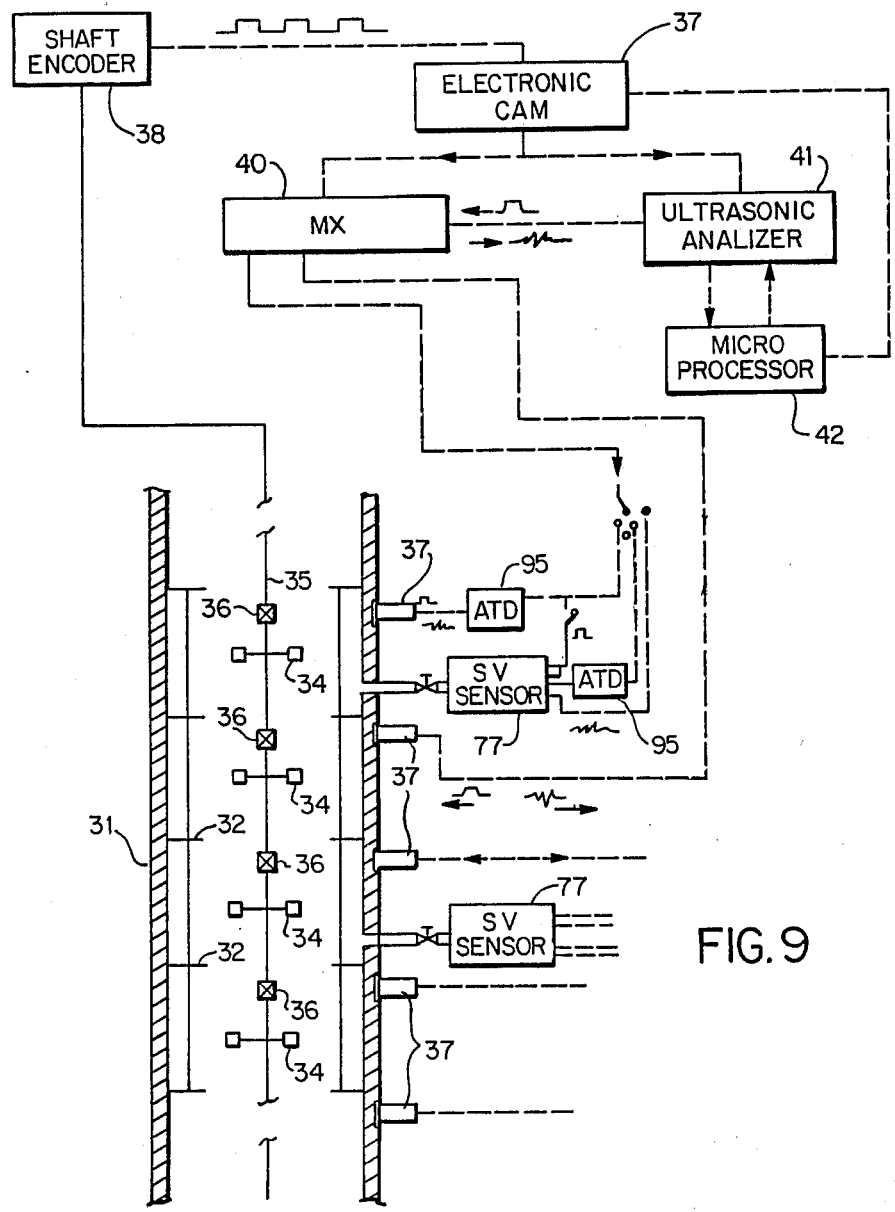
FIG. 9 is a schematic view of an extraction column of a fourth embodiment of this invention.

The structure of the FIG. 9 embodiment is similar to that of FIG. 4, but includes cubes or dice to rotate with the shaft, to reflect the ultrasound pulses in the same manner as in the embodiment of FIG. 3. The same reference numbers as used in FIG. 3 identify similar elements, which need not be described in detail. Similarly to the previously described embodiment of this invention, to determine the velocity of sound $C^*$ in the dispersion inside the column 31, it is necessary to determine the exact length of the sonic path through the liquid dispersion and the exact length of the sonic path through the liquid dispersion as well as the exact value of the overall time delay due to the electronics and the acoustic window, and the predetermined analog time delay.

The determination of these two parameters for each transducer is as described previously in respect to FIG. 3.

The self calibrating feature of this invention requires the knowledge of the velocity of the sound $C_1$ in the continuous phase and the velocity of sound $C_2$ in the dispersed phase in order to calculate $\phi$ using equation 1. This is accomplished in the same manner as in the above embodiment using the differential sonic velocimeters 77.

The procedure to operate the differential sonic velocimeter and the calculation to be performed in the microprocessor to compute values $C_1$, $C_2$ and $\phi$ are identical to those described above. Various AD converters 95 are also indicated.

It is apparent that truly accurate real-time measurement of the holdup $\phi$ at each stage or compartment of the column extractor/reactor 51 requires accurate knowledge of the sound velocities $C_1$ and $C_2$ of the two liquid phases, even as these undergo physical and chemical changes from one stage to the next.

Figure 10:
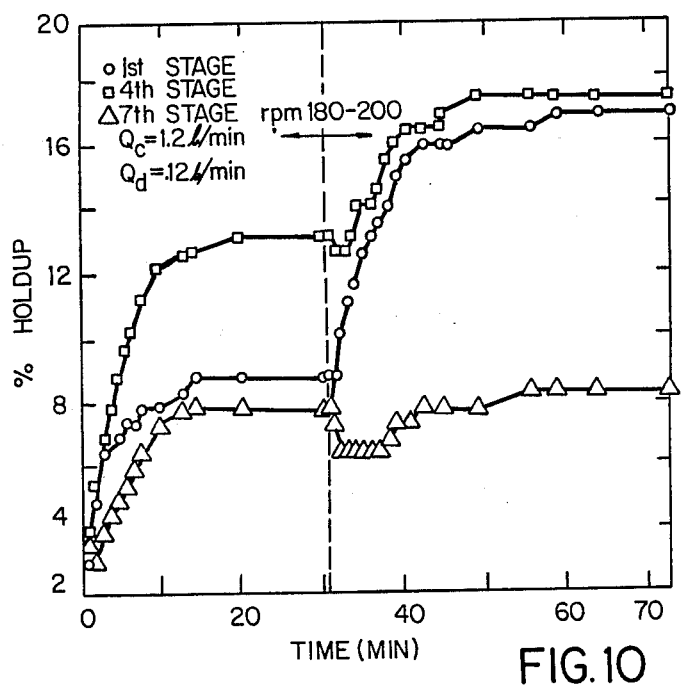
FIG. 10 is a chart of fractional holdup over time for several stages of the reactor.

During extractor/reactor startup, and when parameters change such as rotor speed, feed rates, or temperature, there is a gradual change in holdup $\phi$ at the various stages until the new equilibrium is reached. This start-up time varies of course with the specific gravities and viscosities of the two phases, but generally will be on the order of ten to thirty minutes or longer. The change in percent fractional holdup of xylene in water is shown in the chart in FIG. 10. Here the measurement of holdup $\phi$ is plotted for first, fourth, and seventh stages or compartments 54g, 54d, and 54a. At first, there is a zero holdup, which increases gradually and reaches an equilibrium at about twenty minutes. The speed of the rotor 56 and impellers 55 is increased from 180 to 200 rpm, at the time indicated by the broken vertical line (about 31 minutes). There is initially a small decrease in holdup $\phi$ at the top and bottom compartments, but then a gradual rise in holdup $\phi$ at all levels until a new equilibrium is reached about thirty minutes thereafter.

Figure 11:
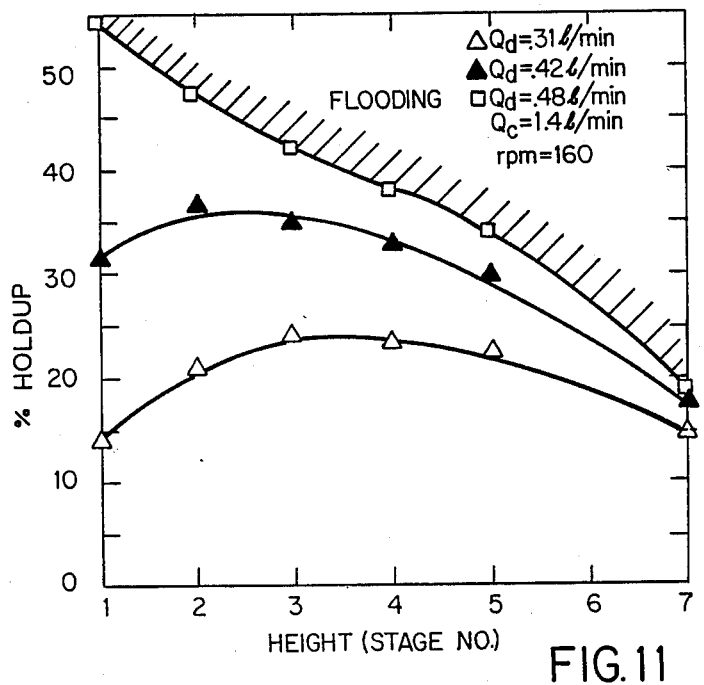
FIG. 11 is a chart of fractional holdup versus stage location for a number of feed rates to the reactor.

Accurate knowledge of the holdup $\phi$ and of changes therein at all levels is required for precise process control, so that optimum throughput can be achieved. As indicated in the chart of FIG. 11, the dispersed phase holdup can be increased by increasing the organic phase feed rate Qd, but only until a point of flooding. There the percentage holdup at equilibrium is shown at six of the seven stages or compartments 54g, 54f, 54e, 54d, 54c, and 54a, corresponding to stages 1–5 and 7 respectively, for three organic feed rates at a constant aqueous feed rate. The "flooding" rate represents the critical level, above which the suspension clogs the reactor and rejects additionally fed dispersion. This can be determined quite precisely with the technique of this invention. By using real time measurements of holdup $\phi$ at all levels, the feed rates can be controlled to keep the holdup safely below the critical threshold.

While this invention has been described in detail with reference to particular embodiments it should be understood that many modifications and variations would be apparent to those of skill in the art without departing from the scope and spirit of the invention, as defined in the appended claims.

What is claimed is:

1. A column reactor of the type in which first and second liquid phases are mixed to form a two-liquid dispersed phase system with one of the liquid phases being held up as a liquid/liquid dispersion in the other liquid phase, including a reactor vessel having a vessel wall within which the two-liquid system is contained, means for introducing the first and second liquids into said vessel, and mixing means for agitating the liquids; vessel ultrasonic transducer means disposed in acoustic communication with the two-liquid dispersed phase system in said vessel for transmitting ultrasonic pulses into said two-liquid dispersed phase system and for receiving said pulses after they have travelled through said two-liquid dispersed phase system over a predetermined path; and means for electrically exciting said vessel transducer means; the improvement comprising a velocimeter that includes a body that is formed of first and second chamber portions, input means that draws said two-liquid system from said vessel and separates the system into said first and second liquids with the first liquid in said first chamber portion and the second liquid in the second chamber portion, means to drain the liquids from the first and second chamber portions, and first and second velocimeter ultrasonic transducer means disposed in acoustic communication with the first and second liquids in the respective chamber portions of said velocimeter body for transmitting ultrasonic pulses into said first liquid and said second liquid and for receiving the pulses after they have travelled through said first liquid and said second liquid over predetermined paths in the first and second velocimeter chamber portions, respectively; means for electrically exciting said first and second velocimeter transducer means to generate said ultrasonic pulses; means for sensing the pulse reception at the respective transducer means; and means for computing the sound velocities $C_1$, $C_2$, and $C^*$ in the first liquid, the second liquid, and said first two liquid system, respectively, from travel times of said ultrasonic pulses and the lengths of the respective predetermined paths, such that a dispersed phase fractional holdup $\phi$ of the two-liquid dispersed phase system can be calculated according to the relationship:

$$\phi = \frac{C_2 (C_1 - C^*)}{C^* (C_1 - C_2)} .$$

2. The reactor of claim 1 in which said vessel includes a column having baffles along its axis to divide the column into at least three compartments, and said velocimeter input means is in fluid communication with at least an intermediate one of said compartments.

3. The reactor of claim 2 in which said vessel includes a second velocimeter having input means coupled to another intermediate one of said compartments, for drawing the two-liquid dispersed system therefrom, and dividing the same into the first liquid and the second liquid, a body that includes a first chamber portion and a second chamber portion, with the first liquid being reposed in the first chamber portion and the second liquid being reposed in the second chamber portion, and said first and second velocimeter ultrasonic transducer means being in acoustic communication with the first and second liquids in the respective chamber portions of the body of the second velocimeter.

4. The reactor of claim 3 wherein there are respective vessel ultrasonic transducer means for each of said compartments, and multiplexing means for connecting the electrically exciting means and the sensing means to the transducer means of the respective vessel compartments and to the transducer means of the respective velocimeters in a predetermined sequence.

5. The reactor of claim 1 wherein the velocimeter input means to draw the two liquid system from the vessel includes first filter means for passing only the first liquid to the first chamber and second filter means for passing only the second liquid to the second chamber.

* * * * *

UNITED STATES PATENT AND TRADEMARK OFFICE
CERTIFICATE OF CORRECTION

PATENT NO. : 4,852,396
DATED : August 1, 1989
INVENTOR(S) : Lawrence L. Tavlarides et al.

It is certified that error appears in the above-identified patent and that said Letters Patent is hereby corrected as shown below:

Col. 12, line 66, please delete "first".

Signed and Sealed this

Twenty-second Day of May, 1990

*Attest:*

HARRY F. MANBECK, JR.

*Attesting Officer*           *Commissioner of Patents and Trademarks*